(12) United States Patent
Kiba et al.

(10) Patent No.: US 10,736,487 B2
(45) Date of Patent: Aug. 11, 2020

(54) MEDICAL OBSERVATION APPARATUS

(71) Applicant: Sony Olympus Medical Solutions Inc., Tokyo (JP)

(72) Inventors: Hiroyuki Kiba, Tokyo (JP); Aki Mizukami, Kanagawa (JP); Noriaki Fujita, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/258,968

(22) Filed: Jan. 28, 2019

(65) Prior Publication Data

US 2019/0269298 A1    Sep. 5, 2019

(30) Foreign Application Priority Data

Mar. 5, 2018  (JP) .................. 2018-038941

(51) Int. Cl.
*A61B 1/05* (2006.01)
*A61B 1/00* (2006.01)
*G02B 23/24* (2006.01)
*G16H 30/40* (2018.01)

(52) U.S. Cl.
CPC ........ *A61B 1/00009* (2013.01); *A61B 1/0002* (2013.01); *A61B 1/00006* (2013.01); *A61B 1/05* (2013.01); *G02B 23/2484* (2013.01); *G16H 30/40* (2018.01)

(58) Field of Classification Search
CPC .............. A61B 1/0002; A61B 1/00009; A61B 1/00006; A61B 1/05; G16H 30/40; G02B 23/2484; H04N 2005/2255
See application file for complete search history.

(56) References Cited

U.S. PATENT DOCUMENTS 5,832,126 A * 11/1998 Tanaka ............... G06T 9/00
382/239
6,603,883 B1 * 8/2003 Hamanaka ......... H04N 19/29
375/240.02
2008/0267516 A1 * 10/2008 Chang ............... H04N 19/597
382/236

(Continued)

FOREIGN PATENT DOCUMENTS

JP    2010-51531    3/2010

*Primary Examiner* — Neil R Mikeska
(74) *Attorney, Agent, or Firm* — Xsensus LLP

(57) ABSTRACT

A medical observation apparatus includes: an imaging unit configured to capture a subject image and output an image signal; a memory unit configured to temporarily store and output the image signal; an abnormality detection unit configured to detect an abnormality in the memory unit; a thinning-out processing unit provided in parallel with the memory unit and configured to perform thinning-out processing on the image signal; a first selector configured to select and output one of the image signals output from the memory unit and from the thinning-out processing unit; an image processing unit configured to perform image processing on the image signal; and a first selection controller configured to control the first selector such that the first selector selects the image signal output from the memory unit when no abnormality is detected and selects the image signal output from the thinning-out processing unit when an abnormality is detected.

9 Claims, 9 Drawing Sheets

(56) References Cited

U.S. PATENT DOCUMENTS

2016/0027159 A1* 1/2016 Amirghodsi .............. G06T 5/30
    382/195
2016/0080687 A1* 3/2016 Matsui ................... H04N 7/014
    386/353

* cited by examiner

MEDICAL OBSERVATION APPARATUS

CROSS-REFERENCE TO RELATED APPLICATION

The present application claims priority to and incorporates by reference the entire contents of Japanese Patent Application No. 2018-038941 filed in Japan on Mar. 5, 2018.

BACKGROUND

The present disclosure relates to a medical observation apparatus for observing a subject.

In the medical field, a medical observation apparatus that images the inside of a subject (inside of a living body), such as a person, and observes the inside of the living body is known (for example, refer to JP 2010-51531 A).

The medical observation apparatus (endoscope system) described in JP 2010-51531 A includes an endoscope that is inserted into a living body and images the inside of the living body and outputs an image signal, a processor device that processes the image signal from the endoscope to generate a video signal for display, and a monitor for displaying a captured image based on the video signal generated by the processor device.

Here, in the processor device, the image signal output from the endoscope is temporarily stored in a memory unit (image data memory), and then various kinds of processing are performed on the image signal read from the memory unit by an image data processing circuit.

SUMMARY

However, in the medical observation apparatus described in JP 2010-51531 A, when an abnormality (abnormality in the memory unit itself, abnormality in control of the memory unit, writing/reading error into/from the memory unit, transmission abnormality of an image signal between the endoscope and the memory unit or between the memory unit and the image data processing circuit, and the like) occurs in the memory unit, an abnormality occurs in the captured image displayed on the monitor. As a result, there is a problem that there is a possibility that observation of the subject may not be continued.

A medical observation apparatus according to one aspect of the present disclosure includes: an imaging unit configured to capture a subject image and output an image signal; a memory unit configured to temporarily store and output the image signal output from the imaging unit; an abnormality detection unit configured to detect an abnormality in the memory unit; a thinning-out processing unit provided in parallel with the memory unit and configured to perform thinning-out processing on the image signal output from the imaging unit and output an image signal subjected to the thinning-out processing; a first selector configured to select and output one of the image signal output from the memory unit and the image signal output from the thinning-out processing unit; an image processing unit configured to perform image processing on the image signal output from the first selector; and a first selection controller configured to control an operation of the first selector such that the first selector selects the image signal output from the memory unit when no abnormality is detected by the abnormality detection unit and the first selector selects the image signal output from the thinning-out processing unit when an abnormality is detected by the abnormality detection unit.

DETAILED DESCRIPTION

Figure 1:
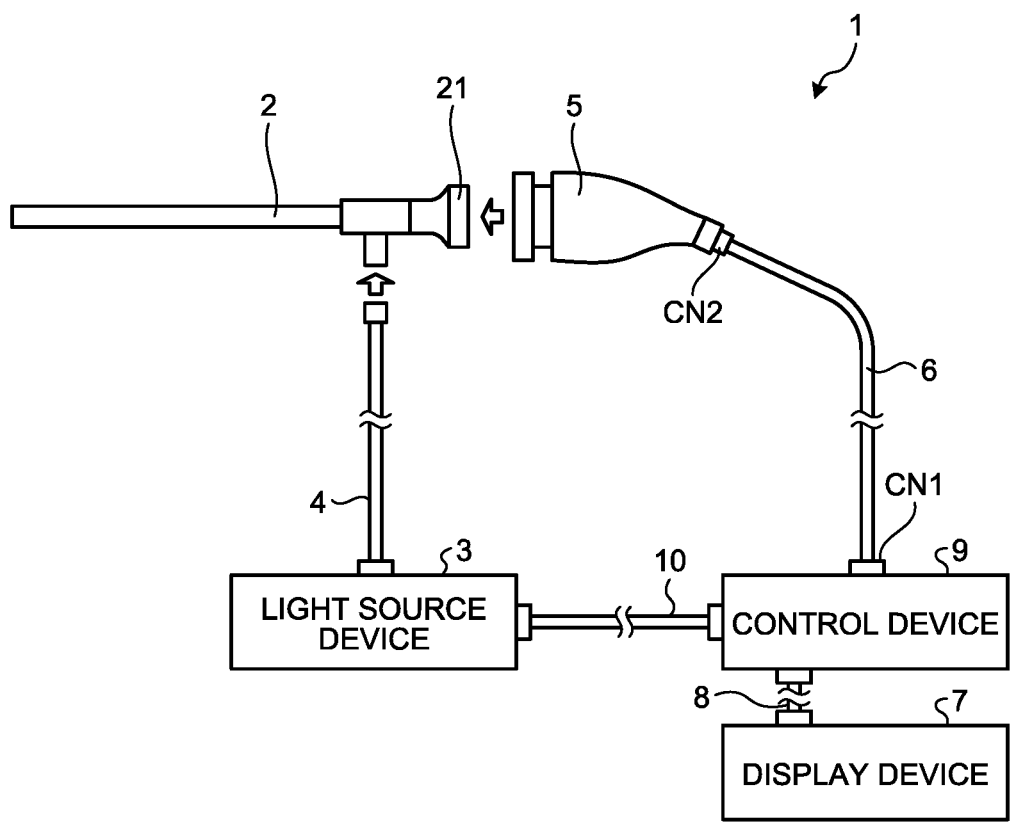
FIG. 1 is a diagram illustrating the schematic configuration of a medical observation apparatus according to an embodiment.

Hereinafter, forms (hereinafter, embodiments) for carrying out the present disclosure will be described with reference to the diagrams. In addition, the present disclosure is not limited by the embodiment described below. In addition, in the description of the diagrams, the same reference numerals are given to the same units.

Schematic Configuration of Medical Observation Apparatus

FIG. 1 is a diagram illustrating the schematic configuration of a medical observation apparatus 1 according to an embodiment.

The medical observation apparatus 1 is an apparatus that is used in the medical field to observe a subject, such as the inside of the living body. As illustrated in FIG. 1, the medical observation apparatus 1 includes an insertion unit 2, a light source device 3, a light guide 4, a camera head 5, a first transmission cable 6, a display device 7, a second transmission cable 8, a control device 9, and a third transmission cable 10.

In the embodiment, the insertion unit 2 is a rigid endoscope. That is, the insertion unit 2 has a rigid or at least partially flexible elongated shape, and is inserted into the living body. In the insertion unit 2, an optical system that is configured by using one or a plurality of lenses and condenses a subject image is provided.

One end of the light guide 4 is connected to the light source device 3, and the light source device 3 supplies light for illuminating the inside of the living body to one end of the light guide 4 under the control of the control device 9.

One end of the light guide 4 is detachably connected to the light source device 3, and the other end of the light guide 4 is detachably connected to the insertion unit 2. Then, the light guide 4 transmits the light supplied from the light source device 3 from one end to the other end to supply the light to the insertion unit 2. The light supplied to the insertion unit 2 is emitted from the distal end of the insertion unit 2 to the inside of the living body. Light (subject image)

that is emitted to the inside of the living body and reflected from the inside of the living body is condensed by the optical system in the insertion unit 2.

The camera head 5 has a function as an imaging unit according to the present disclosure. The camera head 5 is detachably connected to the proximal end (eyepiece unit 21 (FIG. 1)) of the insertion unit 2. Then, under the control of the control device 9, the camera head 5 captures the subject image condensed by the insertion unit 2 and outputs an image signal (RAW signal) by the imaging.

In addition, the detailed configuration of the camera head 5 will be described later.

One end of the first transmission cable 6 is detachably connected to the control device 9 through a connector CN1 (FIG. 1), and the other end of the first transmission cable 6 is detachably connected to the camera head 5 through a connector CN2 (FIG. 1). Then, through the first transmission cable 6, the image signal output from the camera head 5 is transmitted to the control device 9, and a control signal, a synchronization signal, and a clock output from the control device 9, power, and the like are transmitted to the camera head 5.

In addition, the transmission of the image signal from the camera head 5 to the control device 9 through the first transmission cable 6 may be transmission of the image signal using a light signal or may be transmission of the image signal using an electrical signal. Transmission of a control signal, a synchronization signal, and a clock from the control device 9 to the camera head 5 through the first transmission cable 6 is similar.

The display device 7 is configured by using a display using liquid crystal or organic electro luminescence (EL), and displays an image based on the video signal processed by the control device 9.

One end of the second transmission cable 8 is detachably connected to the display device 7, and the other end of the second transmission cable 8 is detachably connected to the control device 9. Then, through the second transmission cable 8, the video signal processed by the control device 9 is transmitted to the display device 7.

The control device 9 is configured to include a central processing unit (CPU) and the like, and performs overall control of the operations of the light source device 3, the camera head 5, and the display device 7.

In addition, the detailed configuration of the control device 9 will be described later.

One end of the third transmission cable 10 is detachably connected to the light source device 3, and the other end of the third transmission cable 10 is detachably connected to the control device 9. Then, through the third transmission cable 10, the control signal from the control device 9 is transmitted to the light source device 3.

Configuration of Camera Head

Next, the configuration of the camera head 5 will be described.

Figure 2:
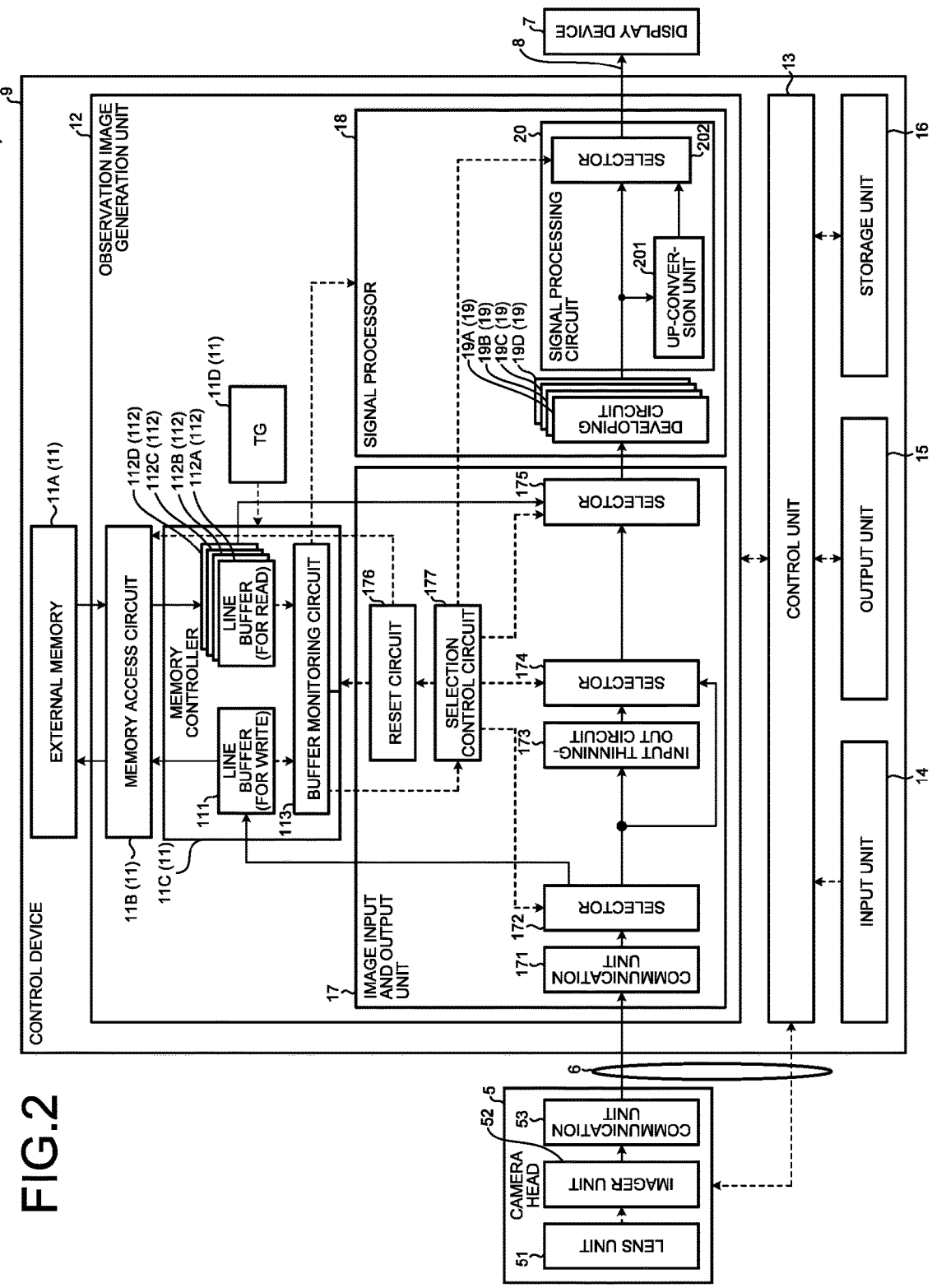
FIG. 2 is a block diagram illustrating the configuration of a camera head and a control device.

FIG. 2 is a block diagram illustrating the configuration of the camera head 5 and the control device 9.

In addition, in FIG. 2, for the sake of convenience of explanation, the connectors CN1 and CN2 between the control device 9 and the camera head 5 and the first transmission cable 6 and connectors between the control device 9 and the display device 7 and the second transmission cable 8 are not illustrated. In addition, in FIG. 2, the flow of the image signal generated by an imager unit 52 is indicated by a solid arrow, and the flow of other signals, such as a control signal, is indicated by a broken arrow.

As illustrated in FIG. 2, the camera head 5 includes a lens unit 51, the imager unit 52, and a communication unit 53.

The lens unit 51 is configured by using one or a plurality of lenses, and forms the subject image condensed by the insertion unit 2 on the imaging surface of the imager unit 52.

The imager unit 52 images the inside of the living body under the control of the control device 9. The imager unit 52 is configured by using a sensor chip in which an imaging element 521 (refer to FIG. 3) such as a charge coupled device (CCD) or a complementary metal oxide semiconductor (CMOS) that receives the subject image condensed by the insertion unit 2 and formed by the lens unit 51 and converts the subject image into an electrical signal, a signal processor (not illustrated) that performs signal processing (A/D conversion or the like) on the electrical signal (analog signal) from the imaging element 521 and outputs an image signal, and the like are integrally formed, and outputs the image signal (digital signal) after A/D conversion. In addition, the above-described signal processor (not illustrated) may be formed as a separate body without being formed integrally with the imaging element 521.

Figure 3:
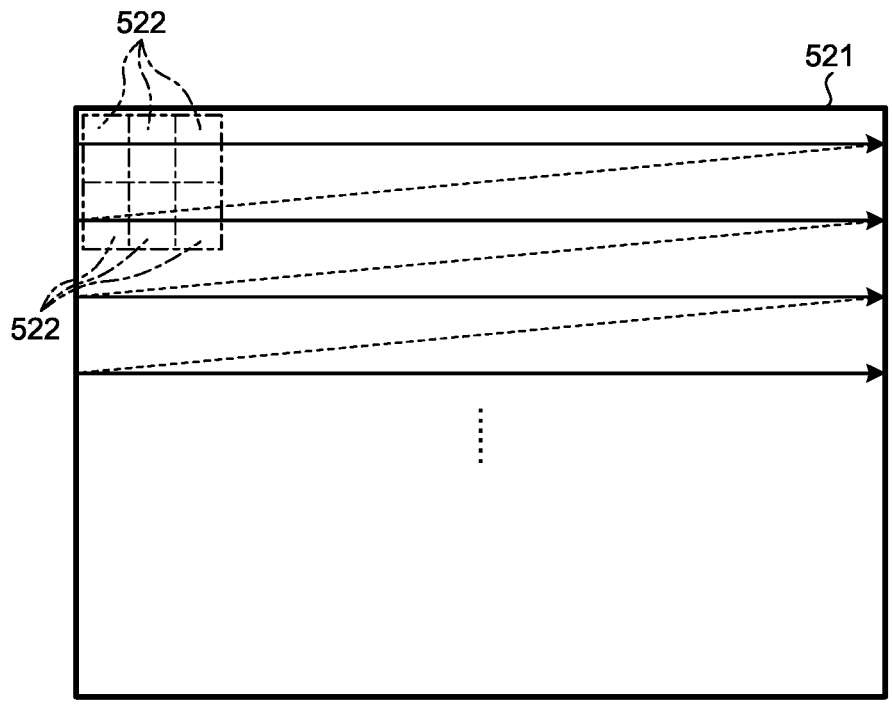
FIG. 3 is a diagram for explaining an image signal output from an imager unit.

FIG. 3 is a diagram for explaining the image signal output from the imager unit 52. Specifically, FIG. 3 is a diagram schematically illustrating the physical arrangement of respective pixels 522 in the imaging element 521.

In addition, in FIG. 3, for the sake of convenience of explanation, only some pixels 522 of all the pixels in the imaging element 521 are illustrated.

The imager unit 52 sequentially outputs the image signals after A/D conversion in raster units. Specifically, in the imaging element 521, the pixels 522 are arranged in a matrix. Then, as illustrated by arrows and broken lines in FIG. 3, the imager unit 52 outputs an image signal of one line from each pixel 522 in a sequential manner from the pixel 522 arranged in the first column to the pixel 522 arranged in the last column among the pixels 522 in the first row. Subsequently, the imager unit 52 outputs an image signal of one line from each pixel 522 in a sequential manner from the pixel 522 arranged in the first column to the pixel 522 arranged in the last column among the pixels 522 in the second row. Then, the imager unit 52 outputs an image signal of one frame by continuing the above-described processing until the last row. When outputting an image signal of the next frame, the imager unit 52 returns to each pixel 522 in the first row to perform the same processing as described above.

The communication unit 53 functions as a transmitter that transmits image signals of raster units, which are sequentially output from the imager unit 52, to the control device 9 through the first transmission cable 6. In the present embodiment, the communication unit 53 is a high-speed serial interface for performing communication of an image signal with the control device 9 through the first transmission cable 6 at a transmission rate of 1 Gbps or higher.

Configuration of Control Device

Next, the configuration of the control device 9 will be described with reference to FIG. 2.

As illustrated in FIG. 2, the control device 9 includes an external memory 11A, an observation image generation unit 12, a control unit 13, an input unit 14, an output unit 15, and a storage unit 16.

The external memory 11A is, for example, a frame memory, such as a dynamic random access memory (DRAM). Then, under the control of the observation image generation unit 12, the external memory 11A temporarily stores image signals of raster units, which are sequentially output from the camera head 5 (communication unit 53), in frame units.

The observation image generation unit 12 generates a video signal for display under the control of the control unit 13. As illustrated in FIG. 2, the observation image generation unit 12 includes a memory access circuit 11B, a memory controller 11C, a timing generator (TG) 11D, an image input and output unit 17, and a signal processor 18.

In addition, the external memory 11A, the memory access circuit 11B, the memory controller 11C, and the TG 11D correspond to a memory unit 11 (FIG. 2) according to the present disclosure.

The TG 11D outputs first and second timing signals to the memory controller 11C. Here, the first timing signal is a signal indicating a write and read start timing Vt (refer to FIGS. 5 and 6) for each frame of the image signal. In addition, the second timing signal is a signal indicating a write and read start timing Ht (refer to FIGS. 5 and 6) for each line of the image signal.

The memory access circuit 11B is a physical layer circuit for accessing the external memory 11A.

The memory controller 11C is a controller circuit of the memory access circuit 11B. As illustrated in FIG. 2, line buffers 111 and 112 and a buffer monitoring circuit 113 are built into the memory controller 11C.

The line buffer 111 is a line buffer for writing into the external memory 11A. That is, under the line buffer control of the memory controller 11C, the image signals of the raster units sequentially output from the camera head 5 (communication unit 53) are temporarily stored in the line buffer 111 for each line according to the first and second timing signals from the TG 11D and then output (written) to the external memory 11A through the memory access circuit 11B.

The line buffer 112 is a line buffer for reading from the external memory 11A. In the present embodiment, as illustrated in FIG. 2, the line buffer 112 is configured to include four first to fourth line buffers 112A to 112D. Then, under the line buffer control of the memory controller 11C, the image signal of one frame temporarily stored in the external memory 11A is temporarily stored in the first to fourth line buffers 112A to 112D for each line through the memory access circuit 11B according to the first and second timing signals from the TG 11D and then sequentially output as first to fourth divided image signals.

Figure 4:
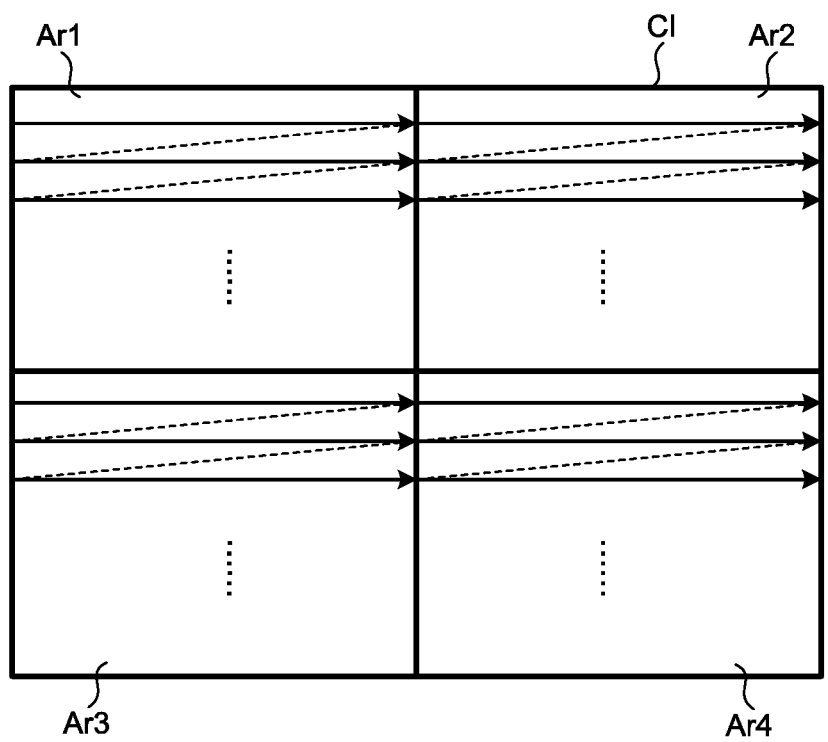
FIG. 4 is a diagram for explaining first to fourth divided image signals output from a memory unit.

FIG. 4 is a diagram for explaining first to fourth divided image signals output from the memory unit 11. Specifically, FIG. 4 illustrates a captured image CI based on an image signal of one frame temporarily stored in the external memory 11A. In addition, in FIG. 4, the entire image region in the captured image CI is divided into four first to fourth regions Ar1 to Ar4. Here, the first region Ar1 is a rectangular region including the upper left corner among the four corners of the captured image CI. The second region Ar2 is a rectangular region including the upper right corner among the four corners of the captured image CI. The third region Ar3 is a rectangular region including the lower left corner among the four corners of the captured image CI. The fourth region Ar4 is a rectangular region including the lower right corner among the four corners of the captured image CI. That is, in FIG. 4, the entire image region in the captured image CI is divided in the shape of a square portion.

Specifically, as indicated by the solid line and the broken line in FIG. 4, in the captured image CI based on the image signal of one frame temporarily stored in the external memory 11A, an image of the first region Ar1 is temporarily stored in the first line buffer 112A for each line at the read start timing Ht (FIG. 5) for each line from the TG 11D and then sequentially output as a first divided image signal. In addition, an image of the second region Ar2 is temporarily stored in the second line buffer 112B for each line at the read start timing Ht for each line from the TG 11D and then sequentially output as a second divided image signal. In addition, an image of the third region Ar3 is temporarily stored in the third line buffer 112C for each line at the read start timing Ht for each line from the TG 11D and then sequentially output as a third divided image signal. In addition, an image of the fourth region Ar4 is temporarily stored in the fourth line buffer 112D for each line at the read start timing Ht for each line from the TG 11D and then sequentially output as a fourth divided image signal.

The buffer monitoring circuit 113 corresponds to an abnormality detection unit according to the present disclosure, and detects an abnormality in the memory unit 11. In the present embodiment, the buffer monitoring circuit 113 monitors the line buffers 111 and 112. In addition, the buffer monitoring circuit 113 detects an abnormality in the memory unit 11 by detecting a reading abnormality (underflow) in the first to fourth line buffers 112A to 112D and a writing abnormality (overflow) in the line buffer 111 by the monitoring. Then, when an abnormality in the memory unit 11 is detected, the buffer monitoring circuit 113 provides error notification to a selection control circuit 177 (FIG. 2) forming the image input and output unit 17.

Figure 5:
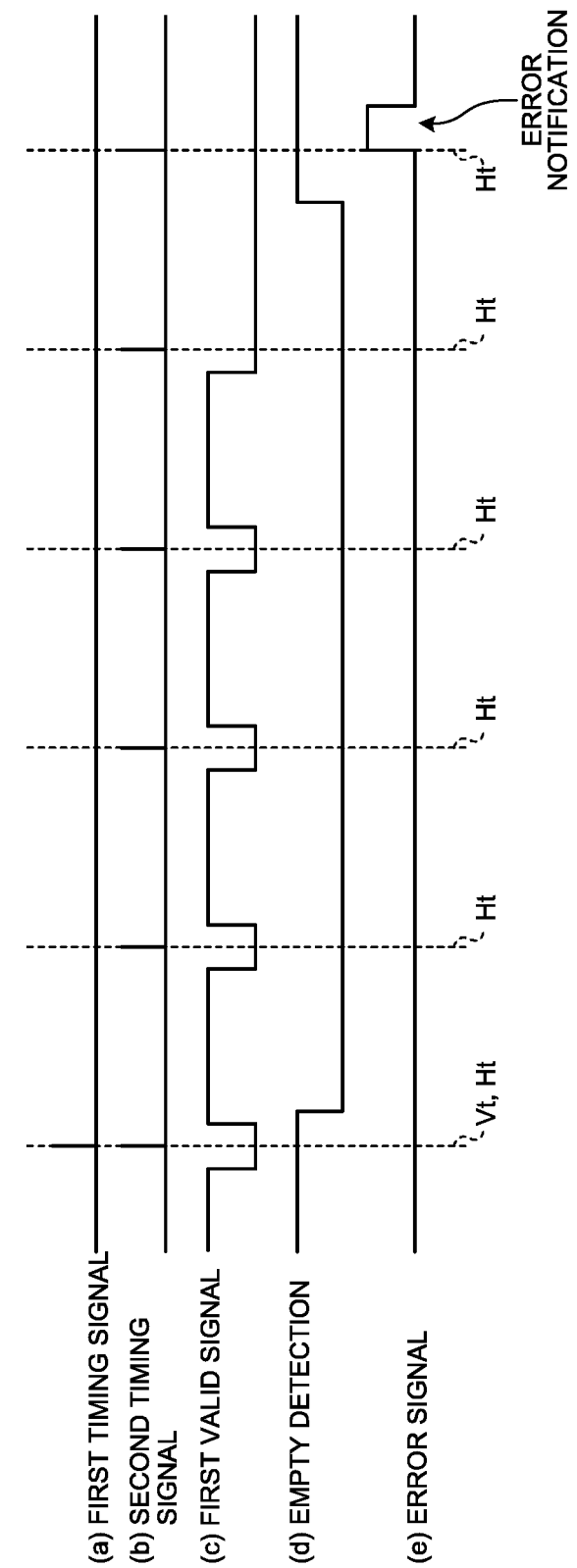
FIG. 5 is a diagram for explaining a reading abnormality in a line buffer.

FIG. 5 is a diagram for explaining a reading abnormality (underflow) in the line buffer 112. In addition, in FIG. 5, for the sake of convenience of explanation, a reading abnormality in one line buffer 112 among the first to fourth line buffers 112A to 112D is described. Here, a part (a) of FIG. 5 illustrates a first timing signal output from the TG 11D. A part (b) of FIG. 5 illustrates a second timing signal output from the TG 11D. A part (c) of FIG. 5 illustrates a first Valid signal that is a monitoring result of the line buffer 112 by the buffer monitoring circuit 113. In addition, the first Valid signal is at a High level while an effective signal (first to fourth divided image signals) is output from the line buffer 112. Then, the first Valid signal is output to the signal processor 18 (developing circuit 19). A part (d) of FIG. 5 illustrates empty detection that is a monitoring result of the line buffer 112 by the buffer monitoring circuit 113. In addition, in the part (d) of FIG. 5, the High level indicates a state in which data (divided image signal (for example, a first divided image signal in the case of the first line buffer 112A)) of the line buffer 112 is empty and data may not be output. A part (e) of FIG. 5 illustrates an error signal output from the buffer monitoring circuit 113. In addition, in the part (e) of FIG. 5, the High level indicates a state in which error notification is provided from the buffer monitoring circuit 113.

As described above, the image signal of one frame temporarily stored in the external memory 11A is temporarily stored in the line buffer 112 for each line at the read start timing Ht (FIG. 5) for each line and then sequentially output as a divided image signal (for example, the first divided image signal in the case of the first line buffer 112A). Here, when the reading from the external memory 11A is delayed for some reason and the data of the line buffer 112 becomes empty at the read start timing Ht of the next one line (when the empty detection illustrated in the part (d) of FIG. 5 is High Level), the buffer monitoring circuit 113 provides error notification that an abnormality (reading abnormality (underflow) in the line buffer 112) has occurred in the memory unit 11 as illustrated in the part (e) of FIG. 5.

Figure 6:
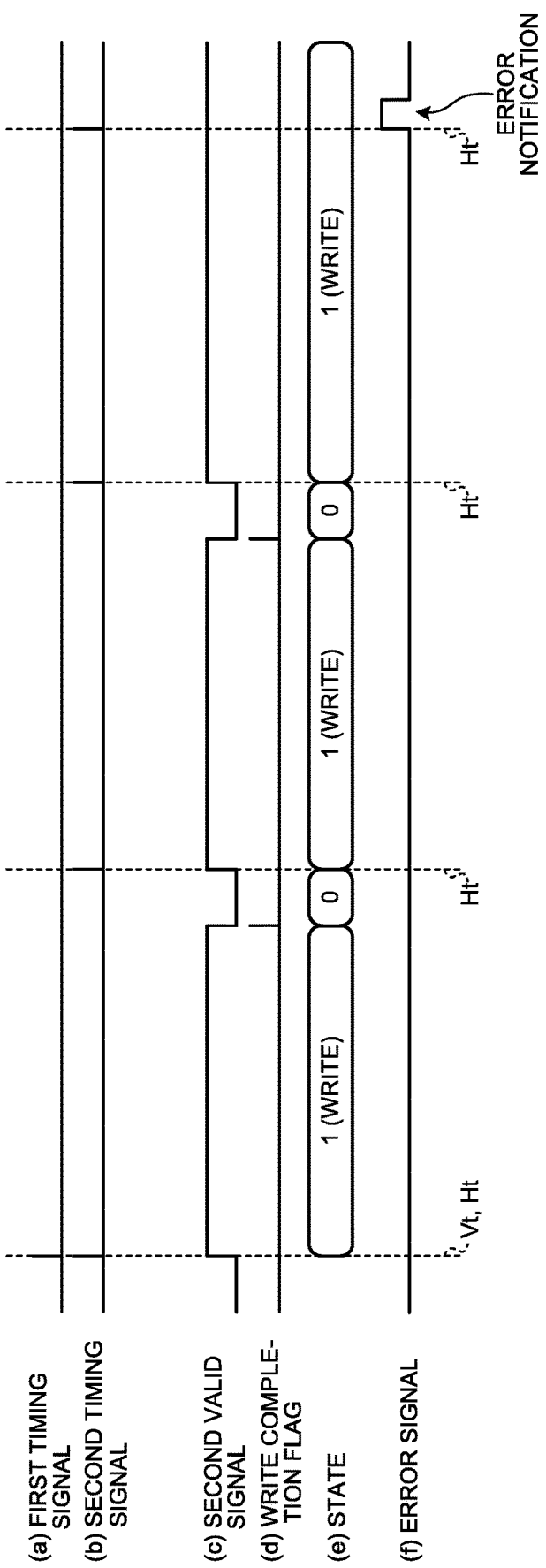
FIG. 6 is a diagram for explaining a writing abnormality in a line buffer.

FIG. 6 is a diagram for explaining a writing abnormality (overflow) in the line buffer 111. Here, a part (a) of FIG. 6 illustrates a first timing signal output from the TG 11D. A part (b) of FIG. 6 illustrates a second timing signal output from the TG 11D. A part (c) of FIG. 6 illustrates a second Valid signal that is a monitoring result of the line buffer 111 by the buffer monitoring circuit 113. In addition, the second Valid signal is at a High level while data (image signal) is being written into the line buffer 111. A part (d) of FIG. 6 illustrates a write completion flag that is a monitoring result of the line buffer 111 by the buffer monitoring circuit 113. In addition, in the part (d) of FIG. 6, the High level indicates a state in which the writing of the image signal of one line into the line buffer 111 is completed. A part (e) of FIG. 6 illustrates a state of the line buffer 111 that is a monitoring result of the line buffer 111 by the buffer monitoring circuit 113. In addition, in the part (e) of FIG. 6, "1" indicates a state during writing. In addition, "0" indicates a state of idle. A part (f) of FIG. 6 illustrates an error signal output from the buffer monitoring circuit 113. In addition, in the part (f) of FIG. 6, the High level indicates a state in which error notification is provided from the buffer monitoring circuit 113.

As described above, the image signals of the raster units sequentially output from the camera head 5 are temporarily stored in the line buffer 111 for each line at the write start timing Ht (FIG. 6) for each line and then output (written) to the external memory 11A. Here, when the writing into the external memory 11A is delayed for some reason and the writing of the data of the line buffer 111 into the external memory 11A is not finished at the write start timing Ht of the next one line (when the state illustrated in the part (e) of FIG. 6 is "1"), the buffer monitoring circuit 113 provides error notification that an abnormality (writing abnormality (overflow) in the line buffer 111) has occurred in the memory unit 11 as illustrated in the part (f) of FIG. 6.

As illustrated in FIG. 2, the image input and output unit 17 includes a communication unit 171, a selector 172, an input thinning-out circuit 173, selectors 174 and 175, a reset circuit 176, and a selection control circuit 177.

The communication unit 171 functions as a receiver that receives image signals of raster units, which are sequentially output from the camera head 5 (communication unit 53), through the first transmission cable 6. In the present embodiment, the communication unit 171 is a high-speed serial interface for performing communication of an image signal with the communication unit 53 at a transmission rate of 1 Gbps or higher.

Under the control of the selection control circuit 177, the selector 172 selects one of the output path to the memory controller 11C (line buffer 111) and the output path to the input thinning-out circuit 173 and the selector 174 as the output path of the image signal received by the communication unit 171.

The input thinning-out circuit 173 corresponds to a thinning-out processing unit according to the present disclosure. The input thinning-out circuit 173 is provided in parallel with the memory unit 11, and performs thinning-out processing on the image signal input through the selector 172 and outputs the image signal after the thinning-out processing.

Here, assuming that the number of divided image signals described above is N (in the present embodiment, N is four of first to fourth divided image signals), the thinning-out processing is processing for changing the total number of pixels of the captured image CI based on the image signal of one frame input through the selector 172 to the number of pixels of 1/N or less (2/N or less in each of horizontal and vertical directions). That is, for example, a 4K image signal is changed to a full-high definition (HD) or lower image signal by thinning-out processing. In addition, in the thinning-out processing, the total number of pixels of the captured image CI may be set to the number of pixels of 1/N or less by deleting the pixels of the captured image CI at predetermined periods, or the total number of pixels of the captured image CI may be set to the number of pixels of 1/N or less by adding adjacent pixels.

Under the control of the selection control circuit 177, the selector 174 selects and outputs one of the image signal output from the input thinning-out circuit 173 and the image signal directly input from the selector 172.

Under the control of the selection control circuit 177, the selector 175 selects either the first to fourth divided image signals output from the first to fourth line buffers 112A to 112D or the image signal output from the selector 174 (one of the image signal output from the input thinning-out circuit 173 and the image signal input to the selector 174 directly from the selector 172). Then, when the first to fourth divided image signals are selected, the selector 175 outputs the first to fourth divided image signals in parallel to the first to fourth developing circuits 19A to 19D (FIG. 2) in the signal processor 18, respectively. In addition, when the image signal output from the selector 174 is selected, the selector 175 outputs the image signal to one of the first to fourth developing circuits 19A to 19D.

The selectors 172, 174, and 175 described above correspond to first and second selectors according to the present disclosure.

The reset circuit 176 corresponds to an initialization unit according to the present disclosure. The reset circuit 176 outputs an initialization instruction to the memory unit 11 (the memory access circuit 11B and the memory controller 11C) under the control of the selection control circuit 177. Then, the memory access circuit 11B and the memory controller 11C execute an initialization sequence in response to the initialization instruction.

The selection control circuit 177 corresponds to first and second selection controllers and an initialization controller according to the present disclosure. The selection control circuit 177 controls the operations of the selectors 172, 174, and 175, a selector 202 (FIG. 2) in the signal processor 18, and the reset circuit 176 according to the error notification from the buffer monitoring circuit 113. In addition, the control unit 13 may control the selection control circuit 177 to control the operations of the selectors 172, 174, 175, and 202 and the reset circuit 176 according to the error notification from the buffer monitoring circuit 113.

As illustrated in FIG. 2, the signal processor 18 includes the developing circuit 19 and a signal processing circuit 20 in which an up-conversion unit 201 and the selector 202 are built.

The developing circuit 19 corresponds to an image processing unit according to the present disclosure. A number of developing circuits 19 corresponding to the number of divided image signals described above are provided. In the present embodiment, as illustrated in FIG. 2, the developing circuit 19 is configured to include four first to fourth developing circuits 19A to 19D. Then, the developing circuit 19 executes the following processing when the first to fourth divided image signals are input from the selector 175 and a case where the image signal through the selector 174 is input from the selector 175.

First, the case where the first to fourth divided image signals are input will be described.

As described above, the first to fourth divided image signals are input in parallel to the first to fourth developing circuits 19A to 19D, respectively. Then, the first to fourth developing circuits 19A to 19D execute various kinds of image processing, such as development processing, noise reduction, color correction, color enhancement, and edge enhancement, in parallel with respect to the first to fourth divided image signals. The first to fourth divided image signals subjected to the image processing are combined and output as a first video signal.

Next, the case where the image signal through the selector 174 is input will be described.

As described above, the image signal through the selector 174 is input to one developing circuit (for example, the first developing circuit 19A) of the first to fourth developing circuits 19A to 19D. Then, one of the developing circuits executes various kinds of image processing, such as development processing, noise reduction, color correction, color enhancement, and edge enhancement, with respect to the image signal to generate a second video signal. That is, three developing circuits other than the one developing circuit do not operate.

For the first video signal or the second video signal output from the developing circuit 19, the up-conversion unit 201 up-converts the resolution of the image based on the video signal under the control of the selection control circuit 177 or the control unit 13.

Under the control of the selection control circuit 177, the selector 202 selects one of the first video signal or the second video signal output from the developing circuit 19 and the first video signal or the second video signal up-converted by the up-conversion unit 201. Then, the selector 202 outputs the selected video signal to the display device 7 through the second transmission cable 8.

For example, when there is no abnormality in the memory unit 11 and a user operation (hereinafter, referred to as an "enlargement operation") for displaying a region of a part of the captured image CI in an enlarged manner is not performed on the input unit 14, signal processing circuit 20 outputs the first video signal output from the developing circuit 19 to the display device 7 as it is without being up-converted. In addition, when there is an abnormality in the memory unit 11 and the thinning-out processing is performed by the input thinning-out circuit 173 or a case where it is desired to increase the resolution by electronic enlargement or the like, the signal processing circuit 20 performs up-conversion and outputs the up-converted video signal to the display device 7. In addition, even when the thinning-out processing is not performed by the input thinning-out circuit 173, for example, 4K may be up-converted into 8K. In this case, this may be strongly performed when the degree of up-conversion is thinned out.

The control unit 13 is configured by using, for example, a CPU, and controls the operations of the camera head 5, the display device 7, and the light source device 3 and controls the operation of the observation image generation unit 12 by outputting control signals through the first to third transmission cables 6, 8, and 10.

In addition, the control unit 13 communicates with the camera head 5 through the first transmission cable 6 to acquire the identification information of the camera head 5. Then, based on the identification information, the control unit 13 determines the number of pixels of the imaging element 521 in the camera head 5 connected to the control device 9. For example, the control unit 13 recognizes the number of pixels corresponding to the identification information with reference to an LUT (look-up table) stored in the storage unit 16. That is, the control unit 13 corresponds to a determination unit according to the present disclosure.

The input unit 14 is configured by using operation devices, such as a mouse, a keyboard, and a touch panel, and receives a user operation. Then, the input unit 14 outputs an operation signal corresponding to the user operation to the control unit 13.

The output unit 15 is configured by using a speaker, a printer, and the like, and outputs various kinds of information under the control of the control unit 13.

The storage unit 16 stores a program executed by the control unit 13, information for processing of the control unit 13, and the like.

Operation of Control Device

Next, the operation of the above-described control device 9 will be described.

Hereinafter, a case where the number of pixels (the number of pixels of the imaging element 521 in the camera head 5 connected to the control device 9) determined by the control unit 13 is equal to or greater than a predetermined threshold value (hereinafter, for the sake of convenience of explanation, the number of pixels is assumed to be 4K) and a case where the number of pixels determined by the control unit 13 is less than the predetermined threshold value (hereinafter, for the sake of convenience of explanation, the number of pixels is assumed to be HD) will be described in order. In addition, for the case where the number of pixels is 4K, a normal case where error notification is not provided by the buffer monitoring circuit 113 and an abnormal case where error notification is provided from the buffer monitoring circuit 113 will be described in order.

Figure 7:
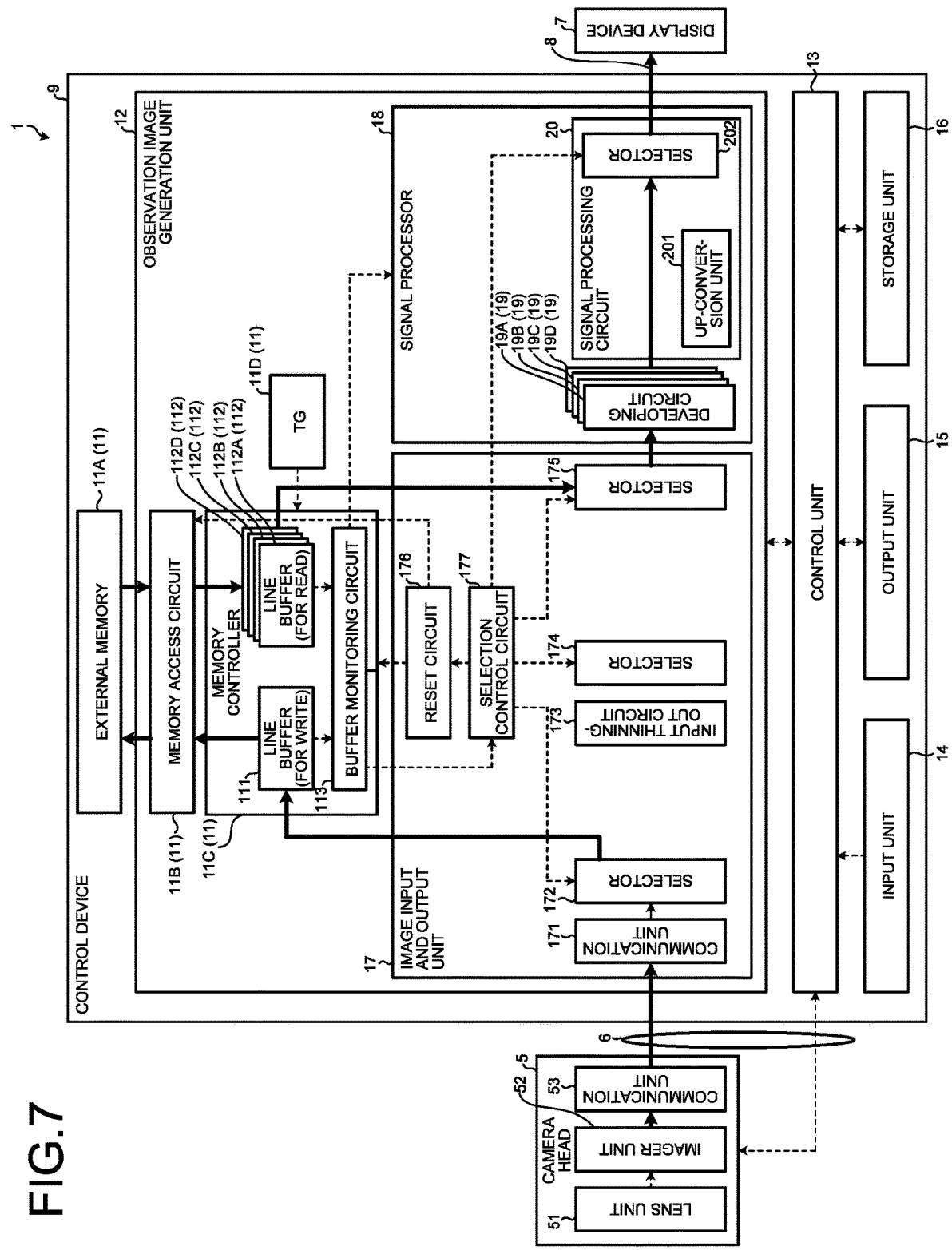
FIG. 7 is a diagram illustrating the flow of an image signal in a normal case where the number of pixels is 4K.
Figure 8:
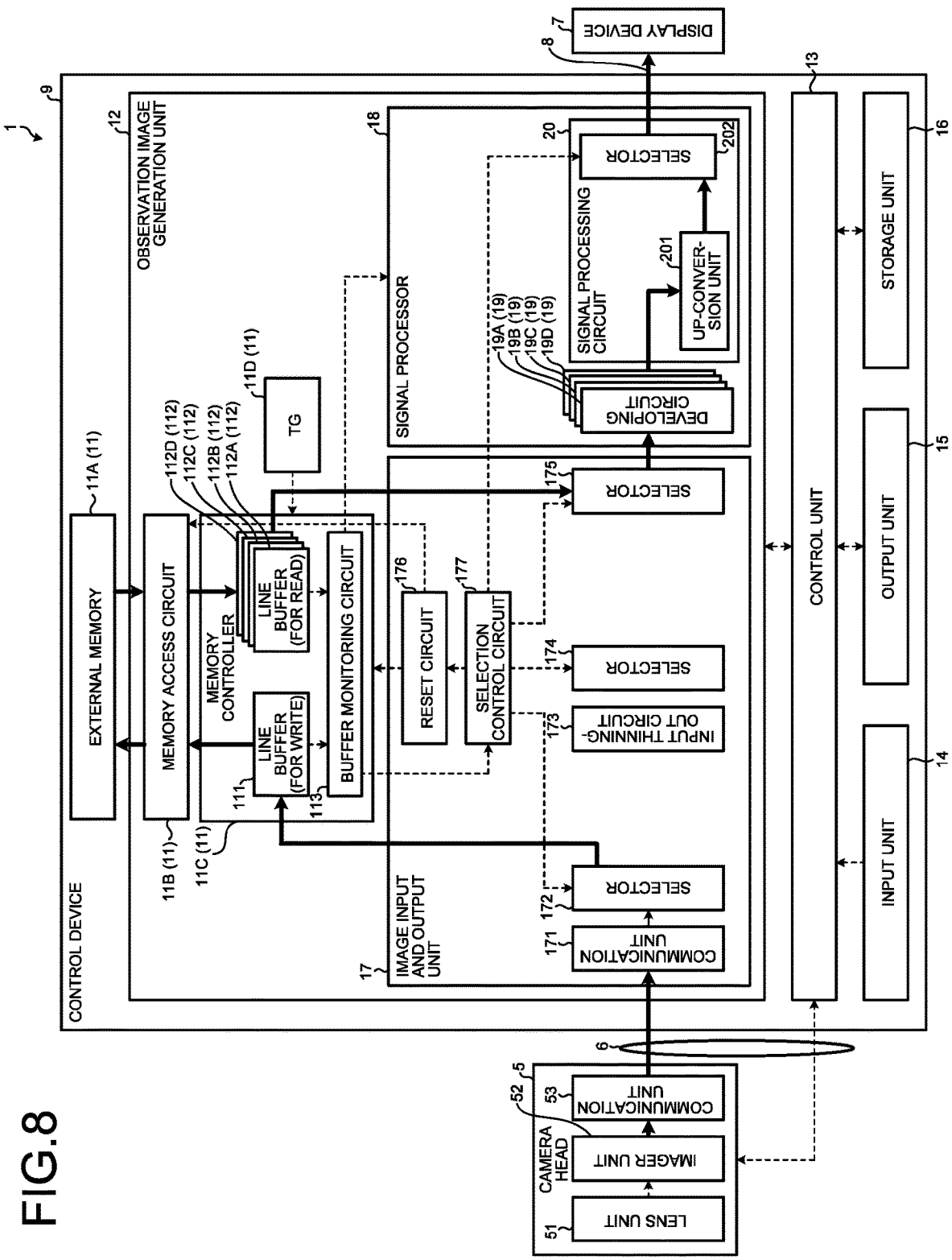
FIG. 8 is a diagram illustrating the flow of an image signal when an output enlargement function is enabled in a normal case where the number of pixels is 4K.

Normal Case Where the Number of Pixels is 4K FIGS. 7 and 8 are diagrams corresponding to FIG. 2, and are diagrams illustrating the flow of the image signal in a normal case where the number of pixels is 4K. In addition, in FIGS. 7 and 8, only the flow of the image signal that actually flows according to the operations of the selectors 172, 174, and 175 and the signal processing circuit 20 is indicated by solid arrows.

When it is determined by the control unit 13 that the number of pixels is 4K and error notification is not provided by the buffer monitoring circuit 113, the observation image generation unit 12 operates as illustrated below under the control of the control unit 13.

The selection control circuit 177 controls the operation of the selector 172 so that the selector 172 selects the output path to the memory controller 11C (line buffer 111) as an output path of the image signal (4K) received by the communication unit 171 as illustrated in FIGS. 7 and 8. As a result, the image signal received by the communication unit 171 is temporarily stored in the external memory 111A in frame units through the memory controller 11C (line buffer 111) and the memory access circuit 11B. In addition, the image signal (4K) of one frame temporarily stored in the external memory 111A is divided into, for example, full-HD first to fourth divided image signals through the first to fourth line buffer 112A to 112D, and each of the first to fourth divided image signals is input to the selector 175.

In addition, the selection control circuit 177 controls the operation of the selector 175 so that the selector 175 selects and outputs the first to fourth divided image signals as illustrated in FIGS. 7 and 8. As a result, the first to fourth divided image signals are input in parallel to the first to fourth developing circuits 19A to 19D, respectively. Then, the first to fourth developing circuits 19A to 19D execute various kinds of image processing in parallel with respect to the first to fourth divided image signals (for example, full-HD first to fourth divided image signals). The first to fourth divided image signals (for example, full-HD first to fourth divided image signals) subjected to the image processing are combined and output as a first video signal (4K).

In addition, FIG. 8 illustrates the flow of the image signal when an enlargement operation is performed. On the other hand, FIG. 7 illustrates the flow of the image signal when the enlargement operation is not performed.

When the enlargement operation is not performed, the selection control circuit 177 controls the operation of the selector 202 so that the selector 202 selects and outputs the first video signal (4K) output from the developing circuit 19 as illustrated in FIG. 7. As a result, the display device 7 displays the captured image CI (4K). That is, when there is no abnormality in the memory unit 11 and the enlargement operation is not performed, the signal processing circuit 20 outputs the first video signal (4K) output from the developing circuit 19 to the display device 7 as it is without allowing the up-conversion unit 201 to function.

On the other hand, when the enlargement operation is performed, the signal processing circuit 20 cuts out a partial region corresponding to the enlargement operation in the captured image CI, and up-converts a first video signal corresponding to the cut region using the up-conversion unit 201. In addition, the selection control circuit 177 controls the operation of the selector 202 so that the selector 202 selects and outputs the first video signal up-converted by the up-conversion unit 201 as illustrated in FIG. 8. As a result, the display device 7 displays an image (4K) corresponding to the partial region described above.

Abnormal Case Where the Number of Pixels is 4K

Figure 9:
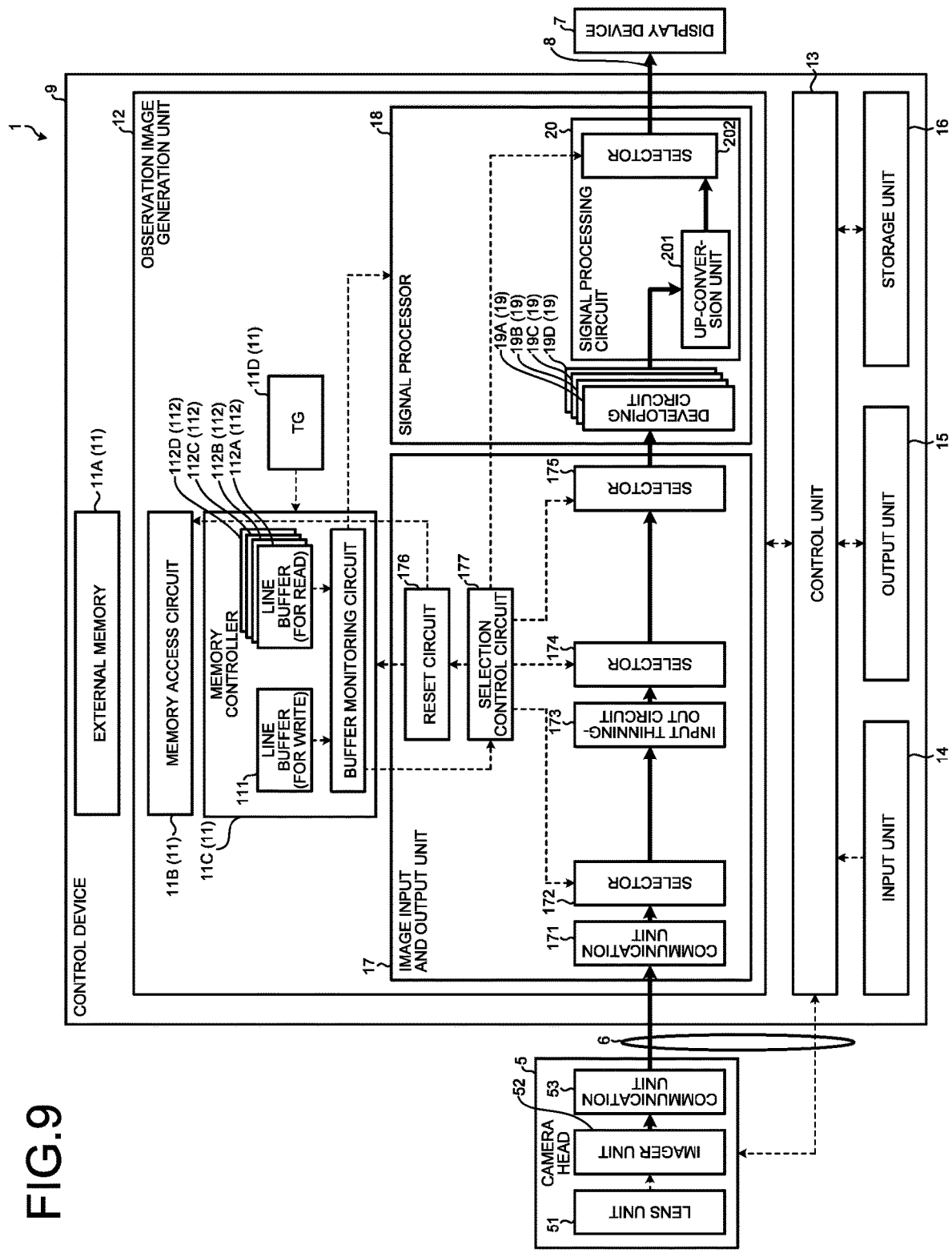
FIG. 9 is a diagram illustrating the flow of an image signal in an abnormal case where the number of pixels is 4K.

FIG. 9 is a diagram corresponding to FIG. 2, and is a diagram illustrating the flow of the image signal in an abnormal case where the number of pixels is 4K. In addition, in FIG. 9, only the flow of the image signal that actually flows according to the operations of the selectors 172, 174, and 175 and the signal processing circuit 20 is indicated by solid arrows.

When it is determined by the control unit 13 that the number of pixels is 4K and error notification has been provided by the buffer monitoring circuit 113, the observation image generation unit 12 operates as illustrated below in response to the error notification from the selection control circuit 177.

The selection control circuit 177 controls the operation of the selector 172 so that the selector 172 selects the output path to the input thinning-out circuit 173 and the selector 174 as an output path of the image signal (4K) received by the communication unit 171 as illustrated in FIG. 9. As a result, the image signal received by the communication unit 171 is input to the input thinning-out circuit 173 so as to be subjected to thinning-out processing. Then, the image signal (4K) is converted into a full-HD image signal, for example.

In addition, the selection control circuit 177 controls the operation of the selector 174 so that the selector 174 selects and outputs the image signal (for example, full HD) output from the input thinning-out circuit 173 as illustrated in FIG. 9.

In addition, the selection control circuit 177 controls the operation of the selector 175 so that the selector 175 selects and outputs the image signal output from the selector 174 (image signal (for example, full HD) output from the input thinning-out circuit 173) as illustrated in FIG. 9. As a result, the image signal (for example, full HD) output from the input thinning-out circuit 173 is input to one developing circuit (for example, the first developing circuit 19A) of the first to fourth developing circuits 19A to 19D. Then, the one developing circuit (for example, the first developing circuit 19A) executes various kinds of image processing on the image signal (for example, full HD) output from the input thinning-out circuit 173 to generate a second video signal (for example, full HD).

In addition, the signal processing circuit 20 up-converts the second video signal (for example, full HD) output from the developing circuit 19 using the up-conversion unit 201. In addition, the selection control circuit 177 controls the operation of the selector 202 so that the selector 202 selects and outputs the second video signal (for example, 4K) up-converted by the up-conversion unit 201 as illustrated in FIG. 9. As a result, the display device 7 displays an image (for example, 4K) corresponding to the second video signal.

In addition, when error notification is provided from the buffer monitoring circuit 113 at normal times (FIGS. 7 and 8), the selection control circuit 177 switches the operations of the selectors 172, 174, 175, and 202 to the states illustrated in FIG. 9 described above at the write and read start timing Vt for each frame of the image signal.

In addition, when error notification is provided from the buffer monitoring circuit 113 at normal times (FIGS. 7 and 8), the selection control circuit 177 controls the operation of the reset circuit 176 to output an initialization instruction to the memory unit 11 (the memory access circuit 11B and the memory controller 11C). Then, the memory access circuit 11B and the memory controller 11C execute an initialization sequence in response to the initialization instruction. At abnormal times (FIG. 9), when the memory unit 11 returns to the normal state from the abnormal state by the initialization sequence (in the case of switching to a state in which error notification is not provided by the buffer monitoring circuit 113), the selection control circuit 177 switches the operations of the selectors 172, 174, 175, and 202 to the states illustrated in FIG. 7 or 8 described above at the write and read start timing Vt for each frame of the image signal. In addition, it is preferable that the switching is performed when error notification is not provided by the buffer monitoring circuit 113 continuously at a predetermined number of timings Vt. For the switching, a circuit that controls the operation under the control of the control unit 13 may be used.

In Case Where the Number of Pixels is HD

Figure 10:
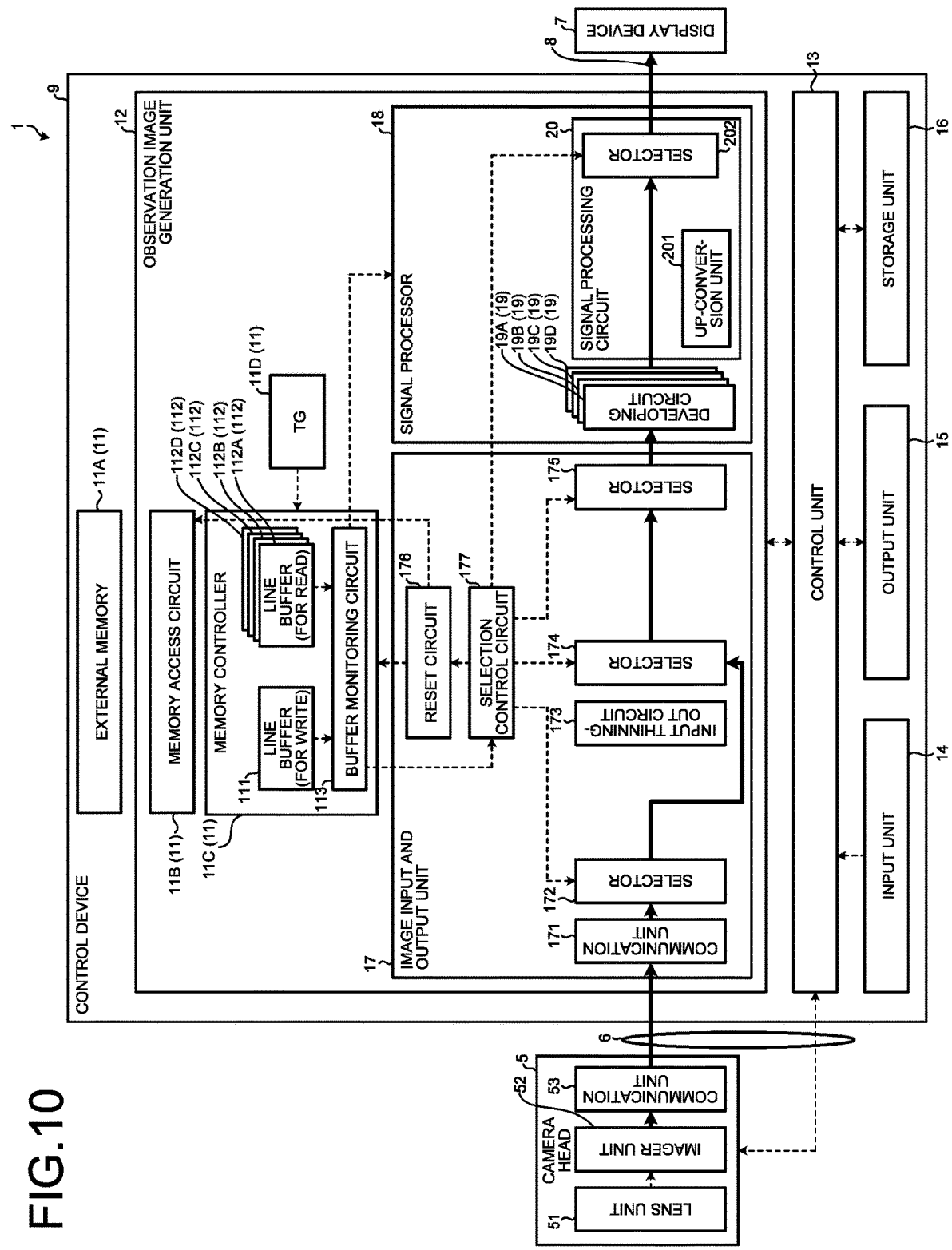
FIG. 10 is a diagram illustrating the flow of an image signal when the number of pixels is HD.

FIG. 10 is a diagram corresponding to FIG. 2, and is a diagram illustrating the flow of the image signal when the number of pixels is HD. In addition, in FIG. 10, only the flow of the image signal that actually flows according to the operations of the selectors 172, 174, and 175 and the signal processing circuit 20 is indicated by solid arrows.

When it is determined by the control unit 13 that the number of pixels is HD, the observation image generation unit 12 operates as illustrated below under the control of the control unit 13.

The selection control circuit 177 controls the operation of the selector 172 so that the selector 172 selects the output path to the input thinning-out circuit 173 and the selector 174 as an output path of the image signal (HD) received by the communication unit 171 as illustrated in FIG. 10. In addition, the selection control circuit 177 controls the operation of the selector 174 so that the selector 174 selects and outputs the image signal directly input from the selector 172. As a result, the image signal (HD) received by the communication unit 171 is input to the selector 175.

In addition, the selection control circuit 177 controls the operation of the selector 175 so that the image signal output from the selector 174 (image signal (HD) received by the communication unit 171) is selected and output as illustrated in FIG. 10. As a result, the image signal (HD) received by the communication unit 171 is input to one developing circuit (for example, the first developing circuit 19A) of the first to fourth developing circuits 19A to 19D. Then, the one developing circuit (for example, the first developing circuit 19A) executes various kinds of image processing on the image signal (HD) received by the communication unit 171 to generate a second video signal (HD).

In addition, the selection control circuit 177 controls the operation of the selector 202 so that the selector 202 selects and outputs the second video signal (HD) output from the developing circuit 19 as illustrated in FIG. 10. As a result, the display device 7 displays an image (HD) corresponding to the second video signal.

According to the present embodiment described above, the following effects may be obtained.

In the medical observation apparatus 1 according to the present embodiment, when no abnormality occurs in the memory unit 11, a former image signal is selected between the image signal output from the camera head 5 and temporarily stored in the memory unit 11 and the image signal output from the camera head 5 and subjected to thinning-out processing by the input thinning-out circuit 173. In addition, image processing is performed on the selected image signal by the developing circuit 19. Then, the captured image CI based on the image signal subjected to the image processing is displayed on the display device 7. On the other hand, in the medical observation apparatus 1, when an abnormality occurs in the memory unit 11, a latter image signal is selected between the image signal output from the camera head 5 and temporarily stored in the memory unit 11 and the image signal output from the camera head 5 and subjected to thinning-out processing by the input thinning-out circuit 173. In addition, image processing is performed on the selected image signal by the developing circuit 19. Then, an image based on the image signal subjected to the image processing is displayed on the display device 7.

Therefore, according to the medical observation apparatus 1 according to the present embodiment, it is possible to obtain the effect that the observation of a subject may be continued even when an abnormality occurs in the memory unit 11.

In addition, in the medical observation apparatus 1 according to the present embodiment, the memory unit 11 divides the image signal of one frame temporarily stored in the external memory 11A into first to fourth divided image signals of the different first to fourth regions Ar1 to Ar4 in the entire image region of the captured image CI based on the image signal and outputs the first to fourth divided image signals. In addition, the developing circuit 19 is configured to include the first to fourth developing circuits 19A to 19D corresponding to the number of divided image signals. Then, the first to fourth developing circuits 19A to 19D perform image processing in parallel with respect to the first to fourth divided image signals.

Therefore, for example, when the image signal output from the camera head 5 is an image signal having a large amount of data, such as 4K or more, at normal times (FIGS. 7 and 8), the image signal having a large amount of data may be divided into four first to fourth divided image signals, and image processing may be executed in parallel on the four first to fourth divided image signals. Accordingly, it is possible to quickly execute image processing and quickly display the captured image CI.

In addition, in the medical observation apparatus 1 according to the present embodiment, assuming that the number of divided image signals is N, the thinning-out processing is processing for changing the total number of pixels of the captured image CI based on the image signal of one frame output from the camera head 5 to the number of pixels of 1/N or less. In addition, in the medical observation apparatus 1, when an abnormality occurs in the memory unit 11, the image signal subjected to the thinning-out processing is subjected to image processing by one of the first to fourth developing circuits 19A to 19D. In addition, in the medical observation apparatus 1, the image signal after the image processing is up-converted by the up-conversion unit 201.

Therefore, for example, when the image signal output from the camera head 5 is an image signal having a large amount of data, such as 4K or more, at abnormal times (FIG. 9), the image signal having a large amount of data may be converted into an image signal having a small amount of data, such as full HD, by thinning-out processing and then image processing may be executed and up-conversion into a 4K image or the like may be performed. Accordingly, even when an abnormality occurs in the memory unit 11 at normal times, it is possible to display an image, which may be visually observed, on the display device 7 so that the observation of the subject may be continued.

In addition, in the medical observation apparatus 1 according to the present embodiment, when an abnormality occurs in the memory unit 11 at normal times (FIGS. 7 and 8), an initialization instruction is output to the memory unit 11, so that the memory unit 11 executes the initialization sequence.

Therefore, when the abnormality in the memory unit 11 is a temporary failure, it is possible to return to the operation at normal times (FIGS. 7 and 8) by the initialization instruction, and it is possible to display the appropriate captured image CI on the display device 7.

In addition, in the medical observation apparatus 1 according to the present embodiment, the operation of the control device 9 is switched to the operation illustrated in FIGS. 7 to 9 or the operation illustrated in FIG. 10 according to the number of pixels of the imaging element 521 in the camera head 5 connected to the control device 9.

Therefore, even when the camera head 5 having the different number of pixels of the imaging element 521 is connected to the control device 9, it is possible to display an appropriate image on the display device 7. That is, it is possible to configure the control device 9 commonly used for various camera heads 5.

Other Embodiments

Although the embodiment for carrying out the present disclosure has been described so far, the present disclosure should not be limited only by the embodiment described above.

In the embodiment described above, the medical observation apparatus 1 is configured by using the rigid endoscope (insertion unit 2). However, the present disclosure is not limited thereto.

For example, the medical observation apparatus according to the present disclosure may be configured by using a flexible endoscope. In addition, the present disclosure may be adopted in a medical observation apparatus (for example, refer to JP-A-2016-42981) that enlarges and images a predetermined field of view of the inside of a subject (inside of a living body) or the surface of a subject (living body surface).

In the embodiment described above, the images of the first to fourth regions Ar1 to Ar4 obtained by dividing the entire image region in the captured image CI in the shape of a square portion are output as the first to fourth divided image signals from the memory unit 11. However, the present disclosure is not limited thereto.

For example, the entire image region in the captured image CI may be divided into first to fourth regions in a shape other than the shape of a square portion, and respective images of the first to fourth regions may be output as first to fourth divided image signals from the memory unit 11. In addition, one region may not be configured by adjacent pixels, and may be a region configured by pixels spaced apart from each other. In addition, the number of divisions (the number of divided image signals, the number of line buffers 112, and the number of developing circuits 19) is not limited to four, and may be other numbers.

In the embodiment described above, the image signal output from the camera head 5 to the control device 9 is the RAW signal. However, the present disclosure is not limited thereto.

For example, some of the various kinds of image processing executed by the developing circuit 19 are executed on the image signal (RAW signal) output from the imaging element 521 in the camera head 5. Then, the camera head 5 outputs the image signal, which has been subjected to some of the various kinds of image processing, to the control device 9.

In the embodiment described above, at least a part of the configuration of the control device 9 may be provided outside (the camera head 5 and the connectors CN1 and CN2) the control device 9.

In the embodiment described above, when the signal processor 18 (developing circuit 19) executes noise reduction, an external memory different from the external memory 11A may be used. In addition, a configuration that causes the signal processor 18 to execute freeze processing (processing for displaying a still image on the display device 7) or superimposition processing (processing for superimposing a captured image corresponding to white light and a captured image corresponding to special light) may be adopted. In addition, when the signal processor 18 executes the freeze processing and the superimposition processing, an external memory different from the external memory 11A may be used.

In the embodiment described above, when error notification is provided from the buffer monitoring circuit 113, a configuration that provides notification of information indicating that an abnormality has occurred in the memory unit 11 (displaying an error message on the display device 7 or the like, outputting an error message from a speaker by voice, or the like) may be adopted.

In the medical observation apparatus according to the present disclosure, when no abnormality occurs in the memory unit, a former image signal is selected between the image signal output from the imaging unit and temporarily stored in the memory unit and the image signal output from the imaging unit and subjected to thinning-out processing by the thinning-out processing unit. In addition, image processing is performed on the selected image signal by the image processing unit. Then, a captured image based on the image signal subjected to the image processing is displayed on the display device. On the other hand, in the medical observation apparatus, when an abnormality occurs in the memory unit, a latter image signal is selected between the image signal output from the imaging unit and temporarily stored in the memory unit and the image signal output from the imaging unit and subjected to thinning-out processing by the thinning-out processing unit. In addition, image processing is performed on the selected image signal by the image processing unit. Then, an image based on the image signal subjected to the image processing is displayed on the display device.

Therefore, according to the medical observation apparatus according to the present disclosure, it is possible to obtain the effect that the observation of a subject may be continued even when an abnormality occurs in the memory unit.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical observation apparatus, comprising:
    a camera to capture a subject image and output an image signal;
    a memory that temporarily stores and outputs the image signal output from the camera; and
    processing circuitry configured to:
    detect an abnormality in the memory;
    select and output one of the image signal output from the memory and the image signal directly from the camera as a selected image signal;
    image processing the selected image signal; and under a condition that no abnormality is detected in the memory, the image signal output from the memory is the selected image signal and, under a condition that an abnormality is detected in the memory, the image signal directly from the camera is the selected image signal.

2. The medical observation apparatus according to claim 1,
    wherein the processing circuitry is configured to output an initialization instruction to the memory under a condition that an abnormality is detected.

3. The medical observation apparatus according to claim 1, wherein the processing circuitry is configured to perform thinning-out processing on the image signal output directly from the camera and output a thinned-out image signal.

4. The medical observation apparatus according to claim 3, wherein
    the memory divides a temporarily stored image signal of one frame into a plurality of divided image signals for a plurality of different regions in an entire image region of a captured image based on the image signal and outputs the divided image signals, and
    the processing circuitry is configured to perform image processing in parallel on the plurality of divided image signals.

5. The medical observation apparatus according to claim 4, wherein
    the processing circuitry is configured to change a total number of pixels of a captured image based on an image signal of one frame to a number of pixels of 1/N or less assuming that a number of the plurality of divided image signals is N, and
    under a condition that an abnormality is detected the processing circuitry is configured to select the thinned-out image signal.

6. The medical observation apparatus according to claim 3, wherein the processing circuitry is configured to up-convert resolution of a captured image based on an the thinned-out image signal.

7. The medical observation apparatus according to claim 3, wherein the processing circuitry is configured to:

determine total number of pixels of a captured image based on an image signal of one frame output from the camera; and thinning-out processing on the image signal output from the camera condition that the total number of pixels is less than a predetermined threshold value.

8. A medical observation apparatus, comprising:

processing circuitry configured to:

detect an abnormality in a memory that stores an image signal from a camera;

select and output one of the image signal output from the memory and the image signal directly from the camera as a selected image signal;

image processing the selected image signal; and under a condition that no abnormality is detected in the memory, the image signal output from the memory is the selected image signal and, under a condition that an abnormality is detected in the memory, the image signal directly from the camera is the selected image signal.

9. A medical observation method, comprising:

detecting an abnormality in a memory that stores an image signal from a camera;

selecting and outputting one of the image signal output from the memory and the image signal directly from the camera as a selected image signal;

image processing the selected image signal; and under a condition that no abnormality is detected in the memory, selecting the image signal output from the memory as the selected image signal and, under a condition that an abnormality is detected in the memory, selecting the image signal directly from the camera as the selected image signal.

* * * * *